(12) United States Patent
Aranyi

(10) Patent No.: US 8,308,042 B2
(45) Date of Patent: Nov. 13, 2012

(54) STRUCTURE FOR ATTACHMENT OF BUTTRESS MATERIAL TO ANVILS AND CARTRIDGES OF SURGICAL STAPLER

(75) Inventor: Ernie Aranyi, Easton, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/108,347

(22) Filed: May 16, 2011

(65) Prior Publication Data

US 2011/0215133 A1    Sep. 8, 2011

Related U.S. Application Data

(63) Continuation of application No. 12/418,763, filed on Apr. 6, 2009, now Pat. No. 7,950,561, which is a continuation-in-part of application No. 11/820,239, filed on Jun. 18, 2007, now Pat. No. 7,665,646.

(51) Int. Cl.
*A61B 17/068* (2006.01)

(52) U.S. Cl. ........... 227/175.1; 227/19; 227/176.1; 227/180.1; 606/139; 606/219

(58) Field of Classification Search ......... 227/19, 227/176.1, 175.1, 180.1, 178.1; 606/151, 606/219, 139, 148
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |
| 5,263,629 A | 11/1993 | Trumbull et al. | |
| 5,314,471 A | 5/1994 | Brauker et al. | |
| 5,344,454 A | 9/1994 | Clarke et al. | |

(Continued)

FOREIGN PATENT DOCUMENTS

DE    1 99 24 311    11/2000

(Continued)

OTHER PUBLICATIONS

International Search Report corresponding to European Application No. EP 10 25 0642.5, completed on Mar. 25, 2011 and mailed on Apr. 4, 2011; 4 pages.

(Continued)

*Primary Examiner* — Scott A. Smith

(57) ABSTRACT

A surgical stapler is provided having a pair of jaws including a staple cartridge and an anvil. Buttress material is releasably secured to at least one of the staple cartridge and the anvil. The buttress material includes a tab to releasably and frictionally engage the at least one of the staple cartridge and the anvil.

19 Claims, 13 Drawing Sheets

U.S. PATENT DOCUMENTS

| | | | |
|---|---|---|---|
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk et al. | |
| 5,468,253 A | 11/1995 | Bezwada et al. | |
| 5,503,638 A | 4/1996 | Cooper et al. | |
| 5,542,594 A | 8/1996 | McKean et al. | |
| 5,549,628 A | 8/1996 | Cooper et al. | |
| 5,575,803 A | 11/1996 | Cooper et al. | |
| 5,653,756 A | 8/1997 | Clarke et al. | |
| 5,683,809 A | 11/1997 | Freeman et al. | |
| 5,690,675 A | 11/1997 | Sawyer et al. | |
| 5,702,409 A | 12/1997 | Rayburn et al. | |
| 5,752,965 A | 5/1998 | Francis et al. | |
| 5,766,188 A | 6/1998 | Igaki | |
| 5,769,892 A | 6/1998 | Kingwell | |
| 5,782,396 A | 7/1998 | Mastri et al. | |
| 5,799,857 A | 9/1998 | Robertson et al. | |
| 5,810,855 A | 9/1998 | Rayburn et al. | |
| 5,814,057 A | 9/1998 | Oi et al. | |
| 5,833,695 A | 11/1998 | Yoon | |
| 5,843,096 A | 12/1998 | Igaki et al. | |
| 5,895,415 A | 4/1999 | Chow et al. | |
| 5,902,312 A | 5/1999 | Frater et al. | |
| 5,908,427 A | 6/1999 | McKean et al. | |
| 5,915,616 A | 6/1999 | Viola et al. | |
| 5,931,847 A | 8/1999 | Bittner et al. | |
| 5,964,774 A | 10/1999 | McKean et al. | |
| 5,997,895 A | 12/1999 | Narotam et al. | |
| 6,019,791 A | 2/2000 | Wood | |
| 6,032,849 A | 3/2000 | Mastri et al. | |
| 6,045,560 A | 4/2000 | McKean et al. | |
| 6,063,097 A | 5/2000 | Oi et al. | |
| 6,080,169 A | 6/2000 | Turtel | |
| 6,099,551 A | 8/2000 | Gabbay | |
| 6,149,667 A | 11/2000 | Hovland et al. | |
| 6,155,265 A | 12/2000 | Hammerslag | |
| 6,210,439 B1 | 4/2001 | Firmin et al. | |
| 6,214,020 B1 | 4/2001 | Mulhauser et al. | |
| 6,241,139 B1 | 6/2001 | Milliman et al. | |
| 6,258,107 B1 | 7/2001 | Balazs et al. | |
| 6,267,772 B1 | 7/2001 | Mulhauser et al. | |
| 6,273,897 B1 | 8/2001 | Dalessandro et al. | |
| 6,280,453 B1 | 8/2001 | Kugel et al. | |
| 6,299,631 B1 | 10/2001 | Shalaby | |
| 6,312,457 B1 | 11/2001 | DiMatteo et al. | |
| 6,312,474 B1 | 11/2001 | Francis et al. | |
| 6,325,810 B1 | 12/2001 | Hamilton et al. | |
| 6,436,030 B2 | 8/2002 | Rehil | |
| 6,454,780 B1 | 9/2002 | Wallace | |
| 6,461,368 B2 | 10/2002 | Fogarty et al. | |
| 6,503,257 B2 | 1/2003 | Grant et al. | |
| 6,514,283 B2 | 2/2003 | DiMatteo et al. | |
| 6,517,566 B1 | 2/2003 | Hovland et al. | |
| 6,551,356 B2 | 4/2003 | Rousseau | |
| 6,592,597 B2 | 7/2003 | Grant et al. | |
| 6,638,285 B2 | 10/2003 | Gabbay | |
| 6,652,594 B2 | 11/2003 | Francis et al. | |
| 6,656,193 B2 | 12/2003 | Grant et al. | |
| 6,669,735 B1 | 12/2003 | Pelissier | |
| 6,677,258 B2 | 1/2004 | Carroll et al. | |
| 6,685,714 B2 | 2/2004 | Rousseau | |
| 6,704,210 B1 | 3/2004 | Myers | |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,773,458 B1 | 8/2004 | Brauker et al. | |
| 6,927,315 B1 | 8/2005 | Heinecke et al. | |
| 6,974,462 B2 | 12/2005 | Sater | |
| 7,128,748 B2 | 10/2006 | Mooradian et al. | |
| 7,147,138 B2 | 12/2006 | Shelton | |
| 7,665,646 B2 | 2/2010 | Prommersberger | 227/175.1 |
| 7,669,747 B2 | 3/2010 | Weisenburgh, II et al. | |
| 7,950,561 B2 * | 5/2011 | Aranyi | 227/175.1 |
| 7,988,027 B2 * | 8/2011 | Olson et al. | 227/175.1 |
| 8,011,550 B2 * | 9/2011 | Aranyi et al. | 227/175.1 |
| 8,011,555 B2 * | 9/2011 | Tarinelli et al. | 227/180.1 |
| 8,083,119 B2 * | 12/2011 | Prommersberger | 227/175.1 |
| 8,157,151 B2 * | 4/2012 | Ingmanson et al. | 227/176.1 |
| 2002/0016626 A1 | 2/2002 | DiMatteo et al. | |
| 2002/0019187 A1 | 2/2002 | Carroll et al. | |
| 2002/0052622 A1 | 5/2002 | Rousseau | |
| 2002/0091397 A1 | 7/2002 | Chen | |
| 2002/0133236 A1 | 9/2002 | Rousseau | |
| 2002/0138152 A1 | 9/2002 | Francis et al. | |
| 2002/0151911 A1 | 10/2002 | Gabbay | |
| 2002/0165559 A1 | 11/2002 | Grant et al. | |
| 2002/0165562 A1 | 11/2002 | Grant et al. | |
| 2002/0165563 A1 | 11/2002 | Grant et al. | |
| 2003/0065345 A1 | 4/2003 | Weadock | |
| 2003/0065346 A1 | 4/2003 | Evens et al. | |
| 2003/0083676 A1 | 5/2003 | Wallace | |
| 2003/0105510 A1 | 6/2003 | DiMatteo et al. | |
| 2003/0114866 A1 | 6/2003 | Ulmsten et al. | |
| 2003/0120284 A1 | 6/2003 | Palacios | |
| 2003/0167064 A1 | 9/2003 | Whayne | |
| 2003/0181927 A1 | 9/2003 | Wallace | |
| 2003/0183671 A1 | 10/2003 | Mooradian et al. | |
| 2003/0208231 A1 | 11/2003 | Williamson, IV et al. | |
| 2004/0034377 A1 | 2/2004 | Sharkawy et al. | |
| 2004/0092960 A1 | 5/2004 | Abrams et al. | |
| 2004/0093029 A1 | 5/2004 | Zubik et al. | |
| 2004/0107006 A1 | 6/2004 | Francis et al. | |
| 2004/0116945 A1 | 6/2004 | Sharkawy et al. | |
| 2004/0142621 A1 | 7/2004 | Carroll et al. | |
| 2004/0172048 A1 | 9/2004 | Browning | |
| 2004/0209059 A1 | 10/2004 | Foss | |
| 2004/0215214 A1 | 10/2004 | Crews et al. | |
| 2004/0215219 A1 | 10/2004 | Eldridge et al. | |
| 2004/0215221 A1 | 10/2004 | Suyker et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1 | 1/2005 | Baily | |
| 2005/0021053 A1 | 1/2005 | Heinrich | |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0118435 A1 | 6/2005 | DeLucia et al. | |
| 2005/0228446 A1 | 10/2005 | Mooradian et al. | |
| 2005/0245965 A1 | 11/2005 | Orban et al. | |
| 2006/0004407 A1 | 1/2006 | Hiles et al. | |
| 2006/0085034 A1 | 4/2006 | Bettuchi | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0212050 A1 | 9/2006 | D'Agostino et al. | |
| 2006/0271104 A1 | 11/2006 | Viola et al. | |
| 2007/0034669 A1 | 2/2007 | de la Torre et al. | |
| 2007/0049953 A2 | 3/2007 | Shimoji et al. | |
| 2007/0179528 A1 | 8/2007 | Soltz et al. | |
| 2007/0203509 A1 | 8/2007 | Bettuchi | |
| 2007/0203510 A1 | 8/2007 | Bettuchi | |
| 2008/0029570 A1 | 2/2008 | Shelton et al. | |
| 2008/0082126 A1 | 4/2008 | Murray et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |

FOREIGN PATENT DOCUMENTS

| | | |
|---|---|---|
| DE | 199 24 311 A1 | 11/2000 |
| EP | 0 594 148 | 4/1994 |
| EP | 1064883 A1 | 1/2001 |
| EP | 1256317 A2 | 11/2002 |
| EP | 1 520 525 | 4/2005 |
| EP | 1 621 141 A21 | 2/2006 |

| | | |
|---|---|---|
| EP | 1 994 890 A1 | 11/2008 |
| EP | 2005894 A2 | 12/2008 |
| WO | WO 90/05489 | 5/1990 |
| WO | WO 96/22055 A1 | 7/1996 |
| WO | WO 97/01989 A1 | 1/1997 |
| WO | WO 98/17180 | 4/1998 |
| WO | WO 99/45849 | 9/1999 |
| WO | WO 03/082126 A1 | 10/2003 |
| WO | WO 03/105698 A2 | 12/2003 |
| WO | WO 2006/023578 | 3/2006 |
| WO | WO 2006/044490 | 4/2006 |
| WO | WO 2006/083748 A1 | 8/2006 |
| WO | WO 2007/121579 A1 | 11/2007 |

OTHER PUBLICATIONS

International Search Report corresponding to European Application No. EP 11 18 8309.6, completed on Dec. 15, 2011 and mailed on Jan. 12, 2012; 3 pages.

International Search Report from application EP 06016962.0 dated Jan. 3, 2007.

International Search Report from Application PCT/US05/36740 mailed Mar. 23, 2007.

International Search Report from Application No. PCT/US2008/002981 dated Jun. 26, 2008.

International Search Report from Application No. EP 08 25 1779 dated Jul. 23, 2008.

European Search Report for EP 10250715.9-2310 date of completion is Jun. 30, 2010 (3 pages).

* cited by examiner

STRUCTURE FOR ATTACHMENT OF BUTTRESS MATERIAL TO ANVILS AND CARTRIDGES OF SURGICAL STAPLER

CROSS REFERENCE TO RELATED APPLICATION

This application is a Continuation Application of U.S. patent application Ser. No. 12/418,763, filed on Apr. 6, 2009, now U.S. Pat. No. 7,950,561, which is a Continuation-in-Part Application of U.S. patent application Ser. No. 11/820,239, filed on Jun. 18, 2007, now U.S. Pat. No. 7,665,646, each of which is incorporated herein by reference.

BACKGROUND

1. Technical Field

The present disclosure relates to attachment systems for staple line buttress materials. More particularly, the present disclosure relates to systems and methods of temporarily attaching staple line buttress materials to an anvil and staple containing cartridge of a surgical stapling instrument.

2. Background of Related Art

Surgical stapling instruments, or "stapling devices", are employed by surgeons to sequentially or simultaneously apply one or more rows of fasteners, e.g., staples or two-part fasteners, to body tissue for the purpose of joining segments of body tissue together. Such devices generally include of a pair of jaws or finger-like structures between which the body tissue to be joined is placed. When the stapling device is actuated, or "fired", longitudinally moving firing bars contact staple drive members in one of the jaws. The staple drive members push the surgical staples through the body tissue and into an anvil in the opposite jaw which crimps the staples closed. If tissue is to be removed or separated, a knife blade can be provided in the jaws of the device to cut the tissue between the lines of staples.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or "buttress" material, between the staple and the underlying tissue. In this method, a layer of buttress material is placed against the tissue and the tissue is stapled in conventional manner. In more recent methods, the buttress material is positioned on the stapling instrument itself prior to stapling the tissue. An exemplary example of this is disclosed in U.S. Pat. No. 5,542,594 to McKean et al. In McKean et al., a tube of buttress material is slipped over the jaw of the stapler. The stapler is then actuated to staple the subject tissue and secure the buttress material between the tissue and staple line to reinforce the tissue and staple line.

Some novel surgical staplers utilize fasteners or clips to temporarily connect buttress material to the jaws of the staplers. However, in some instances, it would be desirable to mold or machine structure into the jaws themselves to facilitate attachment of correspondingly structured buttress materials. It would be further desirable to provide such structure in a manner which does not interfere with the operation of a knife blade associated with the jaws.

SUMMARY

There is disclosed a surgical stapler having a pair of jaws including a staple cartridge and an anvil. At least one of the jaws includes at least two longitudinally extending projections positioned at a first end of the first jaw. The surgical stapler also has a staple line buttress material releasably affixed to the at least one jaw and including recesses for receipt of the at least two projections. In one embodiment each of the at least two projections includes a neck portion and a bulbous portion. In an alternative embodiment, each of the at least two projections is relatively straight. The at least one jaw includes a longitudinally extending knife slot, the at least two projections being separated by the knife slot.

In a further embodiment, the at least one jaw includes two sets of the at least two projections and the at least one jaw includes a longitudinally extending knife slot. The knife slot separates the two sets of the at least two projections.

In particular embodiments, the at least one jaw includes a post at a second end and the buttress material includes a hole for receipt of the post. In a first version, the post is split to allow passage of a knife therebetween, whereas in a second version the post is solid.

In a specific embodiment, the post forms a mushroom shaped protrusion having a cap and the cap defines a flange for engagement with a portion of the buttress material.

In another embodiment the at least one jaw includes a pair of posts and the buttress material includes a pair of holes for receipt of the pair of posts. Each post of the pair of posts is positioned adjacent an outside edge of the buttress material. The at least one jaw also includes a longitudinally extending slot such that the pair of posts are separated by the slot.

In a particular embodiment, the at least one jaw includes a longitudinally extending slot and the post is positioned distally of a distal end of the slot and the buttress material has a hole for receipt of the post. The buttress material further includes a longitudinal slit extending through the area of the buttress material defining the hole.

There is disclosed an end effector of a surgical stapler including having a pair of jaws including a staple cartridge and an anvil, at least one of the jaws including at least one projection extending longitudinally at a first end of the at least one of the jaws and a groove positioned at a second end thereof, and a buttress material releasably affixed to the at least one jaw, the buttress material including at least one aperture at a proximal end for receipt of the at least one projection and a tab at a distal end configured to engage the groove. The tab may be made from a material providing an internal bias or spring action. The at least one projection may be relatively straight with respect to the at least one of the jaws. The at least one projection has a cross-section having a geometry that is suited to secure the at least one projection to the at least one aperture, e.g., a rectangular or a cross-shaped cross-section. Alternatively, the at least one projection may be mushroom shaped. In an embodiment, the at least one projection may include a neck portion and a bulbous head adjacent to the neck portion, the at least one projection adapted to secure the buttress material between the bulbous head and the at least one of the jaws. The at least one projection may be engaged with the least one aperture in an interference fit. A longitudinal slit extending through the at least one of aperture may prevent tearing of the buttress material during insertion of the at least one projection therein. Additionally, the at least one jaw may include a knife slot and the projections and apertures may be positioned to allow passage of a knife therein. The least one jaw may include a pair of the least one projection and the buttress material may include a pair of the least one aperture for reception of the pair of the at least one projection therein. Audible confirmation of proper placement of the buttress retention material on the at least one jaw may be provided.

DESCRIPTION OF THE DRAWINGS

Various embodiments of the presently disclosed interlocking buttress retention systems are disclosed herein with reference to the drawings, wherein.

DETAILED DESCRIPTION OF EMBODIMENTS

Embodiments of the presently disclosed interlocking buttress material retention systems for use with surgical stapling instruments will now be described in detail with reference to the drawings wherein like numerals designate identical or corresponding elements in each of the several views. As is common in the art, the term 'proximal' refers to that part or component closer to the user or operator, i.e. surgeon or physician, while the term "distal" refers to that part or component further away from the user.

Figure 1:
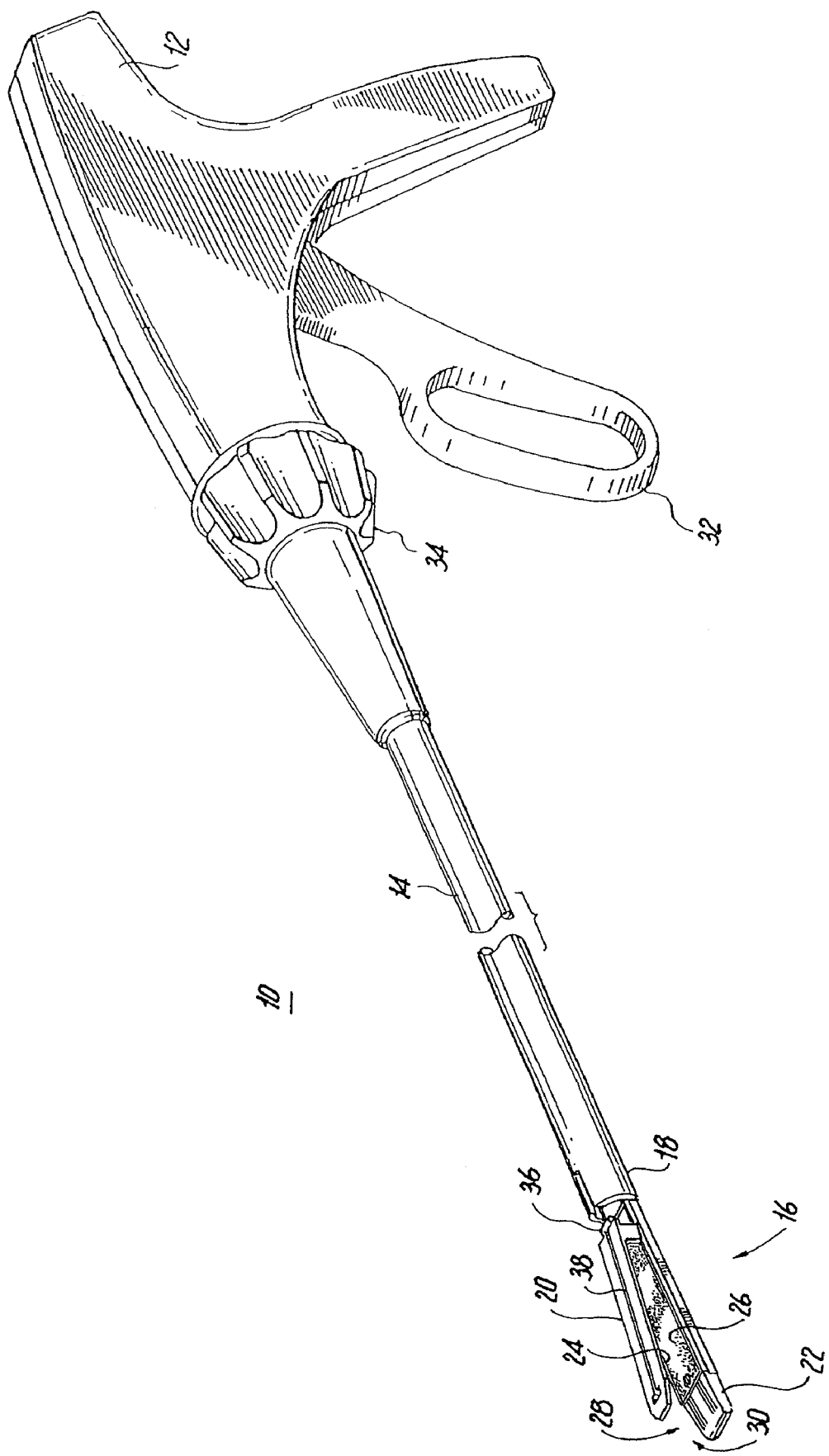
FIG. 1 is a perspective view of a surgical stapling instrument incorporating embodiments of retention systems for attachment of staple line buttress materials to an anvil and staple containing cartridge of the surgical stapling instrument.

Referring now to FIG. 1, there is disclosed a linear surgical stapling instrument or surgical stapler 10 for use in stapling tissue and applying layers of buttress material between the staples and underlying tissue. An exemplary example of this type of surgical stapling instrument is disclosed in U.S. Pat. No. 7,128,253, the entire disclosure of which is incorporated by reference herein. Surgical stapler 10 generally includes a handle 12 having an elongate tubular member 14 extending distally from handle 12. A jaw assembly 16 is mounted on a distal end 18 of elongate tubular member 14. Jaw assembly 16 includes a staple clinching anvil 20 and a staple containing cartridge or staple cartridge 22. Staple cartridge 22 may be permanently affixed to elongate tubular member 14 or may be detachable and thus replaceable with a new staple cartridge 22. Staple clinching anvil 20 is movably mounted on distal end 18 of elongate tubular member 14 and is movable between an open position spaced apart from staple cartridge 22 to a closed position substantially adjacent staple cartridge 22.

Staple clinching anvil 20 is provided with a layer of anvil buttress material 24 and staple cartridge 22 is provided with a layer of cartridge buttress material 26 in the manners described in more detail hereinbelow. An anvil buttress retention system 28 is incorporated into anvil 20 and anvil buttress material 24 and is provided to releasably secure anvil buttress material 24 to staple clinching anvil 20. Likewise, a cartridge buttress retention system 30 incorporated into staple cartridge 22 and cartridge buttress material 26 and is provided to releasably secure cartridge buttress material 26 to staple cartridge 22. Anvil buttress material 24 and cartridge buttress material 26 are provided to reinforce and seal staple lines applied to tissue by surgical stapler 10.

Anvil buttress retention system 28 and cartridge buttress retention system 30 are particularly configured to allow the respective buttress materials to be localized on inwardly facing surfaces of anvil 20 and staple cartridge 22 in order to facilitate passage of surgical stapler 10 into the body of a patient without risk of tearing or wrinkling of the respective buttress materials as surgical stapler 10 is inserted into and manipulated within the body of a patient.

Surgical stapler 10 further includes a trigger 32 movably mounted on handle 12. Actuation of trigger 32 initially operates to move anvil 20 from the open to the closed position relative to staple cartridge 22 and subsequently actuate surgical stapler 10 to apply lines of staples to tissue. In order to properly orient jaw assembly 16 relative to the tissue to be stapled, surgical stapler 10 is additionally provided with a rotation knob 34 mounted on handle 12. Rotation of rotation knob 34 relative to handle 12 rotates elongate tubular member 14 and jaw assembly 16 relative to handle 12 so as to properly orient jaw assembly 16 relative to the tissue to be stapled.

Figure 2:
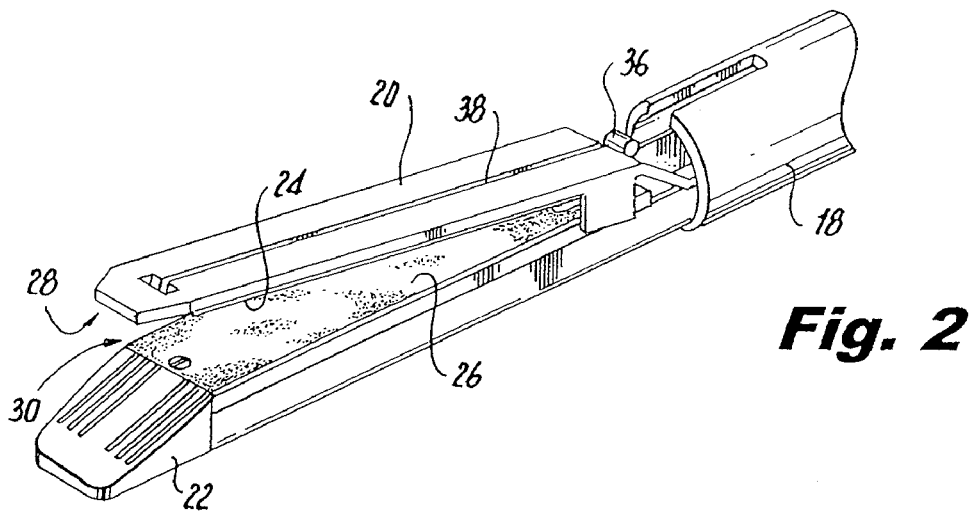
FIG. 2 is a enlarged perspective view of the distal end of the surgical stapling instrument of FIG. 1.

Referring to FIGS. 1 and 2, a driver 36 is provided to move anvil 20 between the open and closed positions relative to staple cartridge 22. Driver 36 moves between a longitudinal slot 38 formed in anvil 20. A knife blade (not shown) is associated with driver 32 to cut tissue captured between anvil 20 and staple cartridge 22 as driver 36 passes through slot 38.

Figure 3:
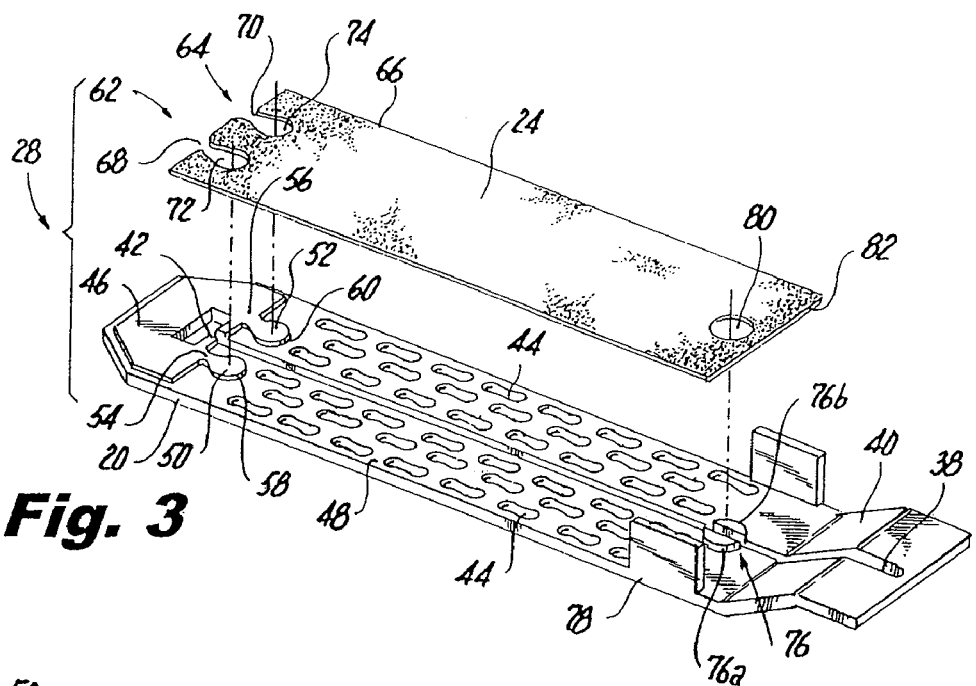
FIG. 3 is a perspective view, with parts separated, of one embodiment of an anvil and buttress material retention system.
Figure 4:
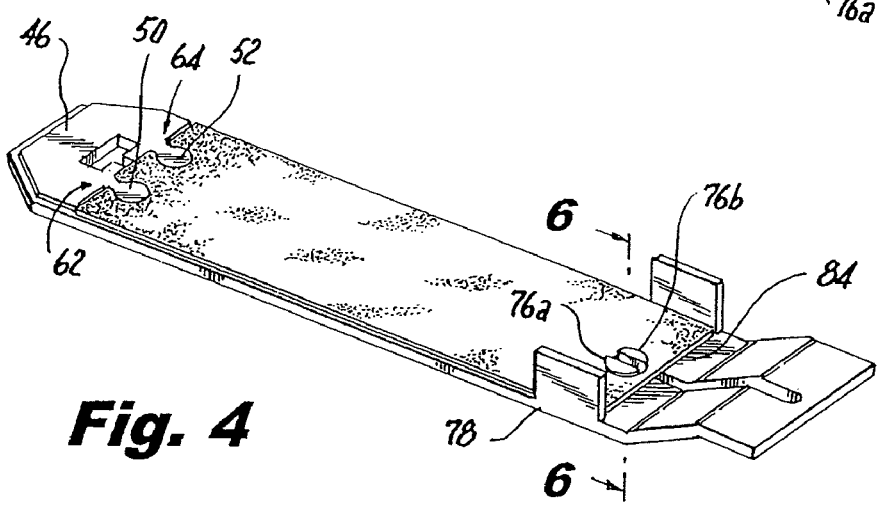
FIG. 4 is a perspective view of the assembled anvil buttress material retention system.

Referring to FIG. 3, in order to move anvil 20 between the open and closed positions, anvil 20 includes a proximal, angled or sloped edge 40 configured to be engaged by driver 36 in order to cam anvil 20 to the closed position. Slot 38 extends distally from sloped edge 40 and terminates in a transverse slot 42 which is configured to capture driver 36 upon complete actuation of surgical stapler 10 to prevent any further actuation of surgical stapler 10. In order to secure staples provided by staple cartridge 22 about the tissues and buttress materials, anvil 20 is provided with longitudinally extending rows of staple clinching pockets 44 located on either side of longitudinal slot 38.

Referring still to FIG. 3, anvil buttress retention system 28, incorporated into anvil 20 and anvil buttress material 24, will now be described. Anvil buttress material 24, as well as cartridge buttress material 26. The buttress material for the staple cartridge 22 and/or anvil 20 may be made from any biocompatible natural or synthetic material. The material from which the buttress material is formed may be bioabsorbable or non-bioabsorbable. It should of course be understood that any combination of natural, synthetic, bioabsorbable and non-bioabsorbable materials may be used to form the buttress material.

Some non-limiting examples of materials from which the buttress material may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the buttress material. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material.

The buttress material may be porous or non-porous, or combinations of porous and non-porous layers. Where the buttress material is non-porous, buttress material may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like.

In embodiments, the buttress material is porous and possesses hemostatic properties. Where the buttress material is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where the buttress material is porous, the pores may be formed using any method suitable to forming a foam or sponge including, but not limited to the lyophilization or freeze-drying of a composition. Suitable techniques for making foams are within the purview of those skilled in the art. Porous buttress materials can be at least 0.2 cm thick, in embodiments from about 0.3 to about 1.5 cm thick. Porous buttress materials can have a density of not more than about 75 mg/cm$^2$ and, in embodiments below about 20 mg/cm$^2$. The size of the pores in the porous buttress materials can be from about 20 μm to about 300 μm, in embodiments from about 100 μm to about 200 μm.

The buttress material may also include a reinforcement member. The reinforcement member may be associated with a porous or non-porous layer or may be positioned between a non-porous layer and a porous layer of the buttress material. Alternatively, the reinforcement member may be positioned entirely within one or more of the individual layers (i.e., embedded within the porous layer, the non-porous layer, or both) of the buttress material. It is also envisioned that the reinforcement member may be positioned at the surface of one of the layers making up the buttress material and, in embodiments, may be positioned at an exterior surface of the buttress material.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the buttress material has randomly oriented chopped fibers that have not been previously fused together embedded within in the buttress material.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly (vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the buttress material in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons ($\beta$-IFN, ($\alpha$-IFN and $\gamma$-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 5:
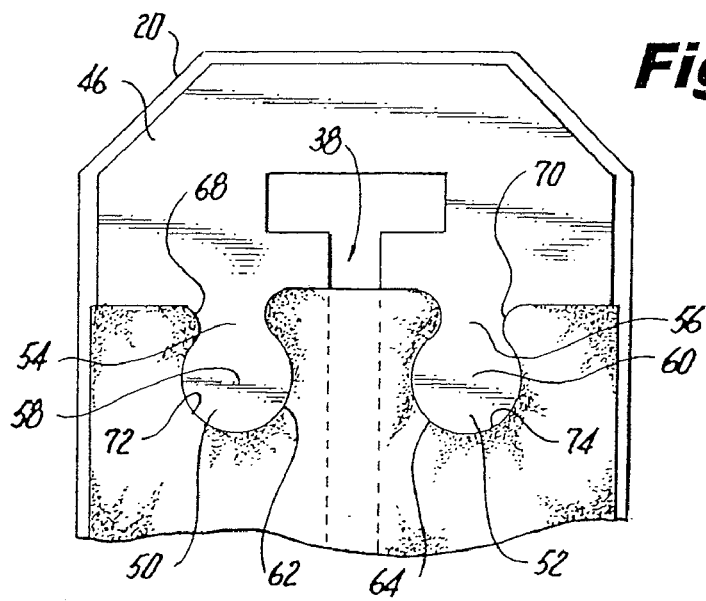
FIG. 5 is a top view of the distal end of the anvil buttress material retention system of FIG. 4.
Figure 6:
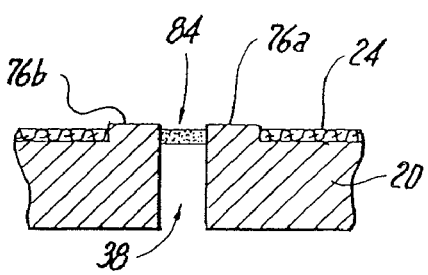
FIG. 6 is a cross-sectional view taken along line 6-6 of FIG. 4.

Anvil buttress retention system 28 is provided to releasably secure anvil buttress material 24 to anvil 20 prior to stapling to tissue. Anvil buttress retention system 28 includes a distally raised region 46 formed on an undersurface 48 of anvil 20. As best shown in FIGS. 3 and 5, distally raised region 46 includes a pair of proximally extending fingers or projections 50 and 52 configured to releasably secure a distal end of anvil buttress material 24 on anvil 20. As used herein, the term "projections" refer to those structures provided on the jaws of the instrument which resemble fingers and are configured to engage buttress material positioned between the fingers in friction fit fashion. Projections 50 and 52 include respective necks 54, 56 and bulbous portions 58, 60 extending proximally from necks 54 and 56. Cut outs 62 and 64 are provided in a distal end 66 of anvil 20 for engagement with projections 50 and 52 of anvil 20. Cut outs 62 and 64 are configured with respective necks 68, 70 and bulbous portions 72 and 74 corresponding to necks 54, 56 and bulbous portions 58, 60 of anvil 20. Projections 50 and 52 along with cutouts 62 and 64 form pairs of interlocking fingers to hold anvil buttress material 24 on anvil 20.

Anvil buttress system 28 further includes a post 76 formed at a proximal end 78 of anvil 20. Anvil buttress material 24 is provided with a hole 80 at a proximal end 82 which is configured to engage post 76 and maintain anvil buttress material 24 taut across undersurface 48 of anvil 20.

As best shown in FIG. 3-6, post 76 is split into post halves 76a and 76b defining a channel 84 therebetween. Channel 84 corresponds to slot 38 in anvil 20 and allows for movement of driver 36, as well as the knife associated with driver 36, through slot 38 to close anvil 20 and cut anvil buttress material 24 in half after stapling.

Referring back for the moment to FIGS. 3 and 4, in order to assemble anvil buttress material 24 to anvil 20 using anvil buttress retention system 28, cut outs 62 and 64 at distal end 66 of anvil buttress material 24 are positioned over projections 50 and 52 on distally raised region 46 of anvil 20. Thereafter, anvil buttress material 24 is drawn taut proximally and hole 80 is positioned over post 76 at proximal end 78 of anvil 20 to secure anvil buttress material 24 against undersurface 48 of anvil 20.

Figure 7:
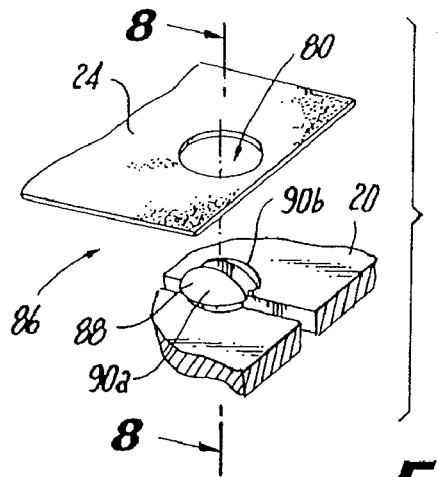
FIG. 7 is a perspective view, with parts separated, of the proximal end of the anvil buttress retention system of FIG. 4.
Figure 8:
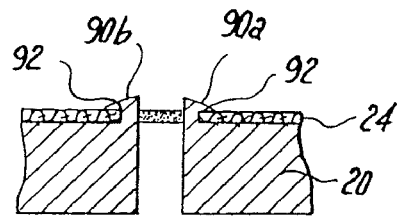
FIG. 8 is a cross-sectional view taken along line 8-8 of FIG. 7.

Referring to FIGS. 7 and 8, there is disclosed an alternative embodiment of a retention system 86 for securing proximal end 82 of anvil buttress material 24 to anvil 20 in a manner to allow passage of driver 36 through slot 38 in anvil 20. Retention system 86 includes a mushroom shaped post or protrusion 88 having an enlarged cap 90 for placement through hole 80 in anvil buttress material 24. Cap 90 defines an underside surface or flange 92 configured to engage anvil buttress material 24. Similar to post 76 described hereinabove, protrusion 88 is split into protrusion halves 88a and 88b defining a slot 94 therebetween for passage of driver 36 and an associated knife blade. Cap 90 assists in preventing premature release of proximal end 82 of anvil buttress material 24. While not specifically shown, the area around hole 80 may include a perforated area to facilitate separation of anvil buttress material 24 from protrusion 88.

Figure 9:
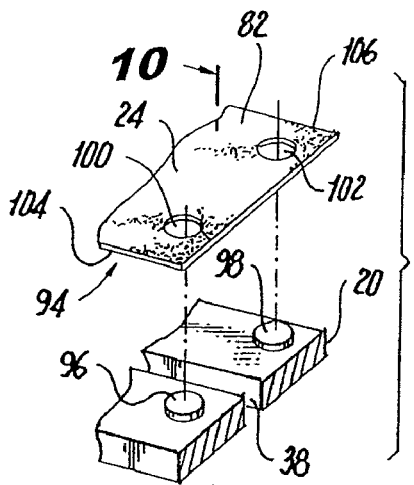
FIG. 9 is a perspective view, with parts separated, of an alternative embodiment of the proximal end of an anvil buttress retention system.
Figure 10:
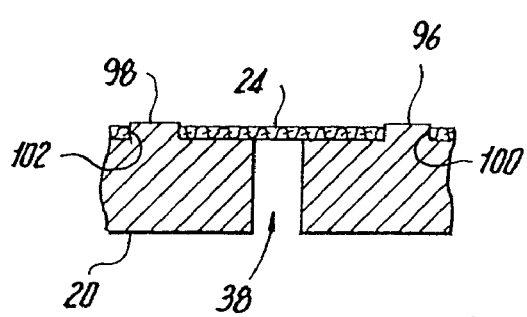
FIG. 10 is a cross-sectional view taken along line 10-10 of FIG. 9.

Referring to FIGS. 9 and 10, there is illustrated a further alternative embodiment of a retention system 94 for retaining proximal end 82 of anvil buttress material 24 on anvil 20. Anvil 20 is provided with a pair of horizontally spaced apart posts 96 and 98 positioned on either side of slot 38. Proximal end 82 of anvil buttress material 24 is provided with a pair of corresponding holes 100 and 102 configured to be engaged by posts 96 and 98, respectively. Posts 96 and 98 locate the area securing anvil buttress material 24 outwardly of slot 38 in anvil 20. This assists in maintaining outer edges 104 and 106 of anvil buttress material 24 taut during use of surgical stapler 10.

Figure 11:
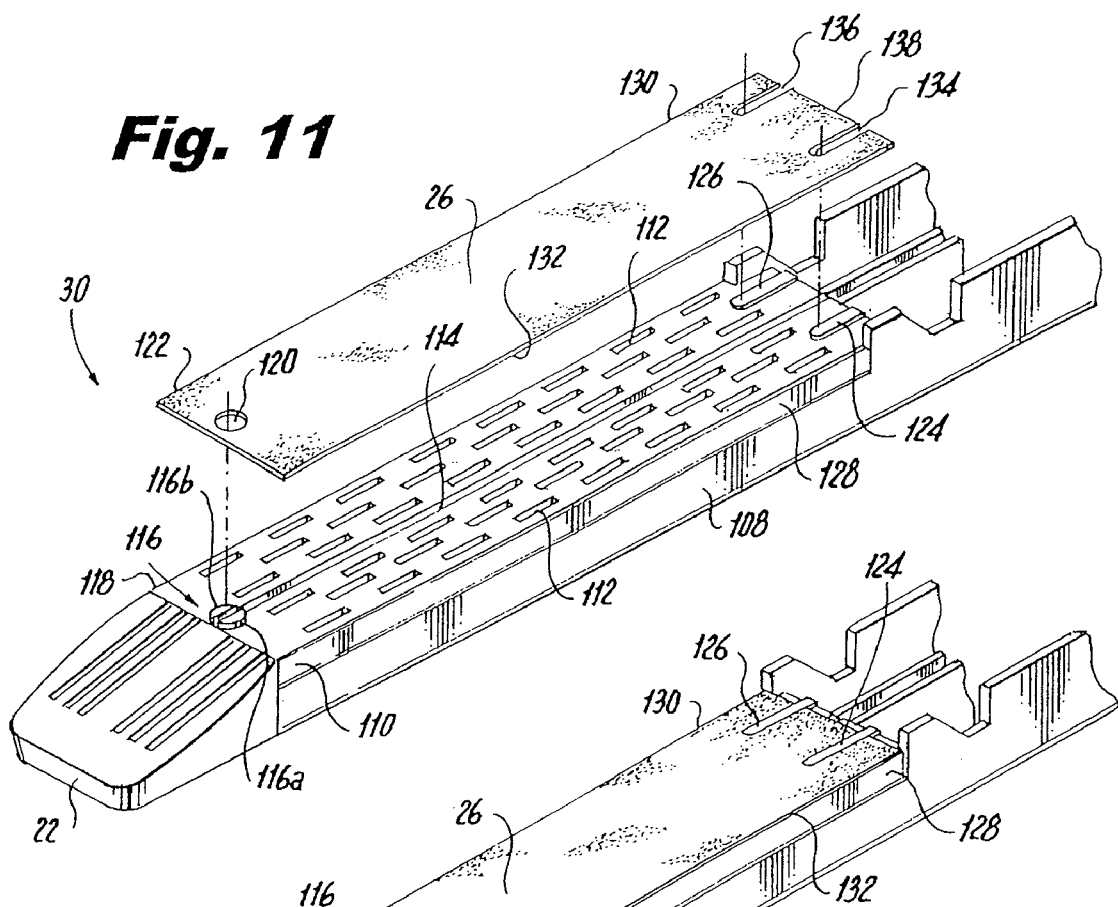
FIG. 11 is a perspective view, with parts separated, of one embodiment of a staple containing cartridge and buttress material retention system.
Figure 12:
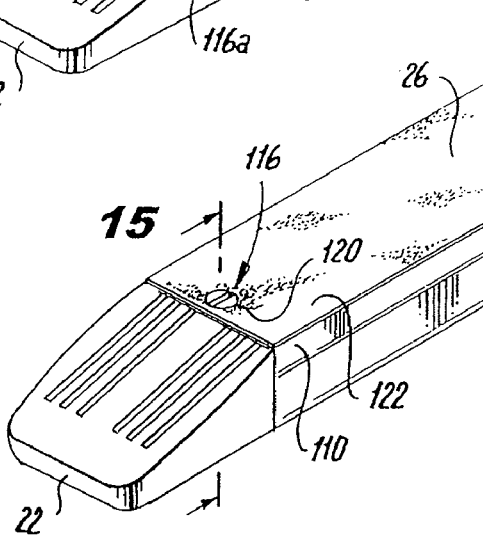
FIG. 12 is a perspective view of the assembled cartridge buttress retention system of FIG. 11.

Referring now to FIGS. 11 and 12, cartridge buttress retention system 30 will now be described. As noted hereinabove, cartridge buttress retention system 30 is provided to retain cartridge buttress material 26 on staple cartridge 22 prior to stapling of tissue. Staple cartridge 22 generally includes a U-shaped outer channel 108 surrounding a staple containing insert 110. Staple containing insert 110 is provided with rows of staple pockets 112, the function of which is described in more detail hereinbelow. A knife channel 114 passes longitudinally through staple containing insert 110 between rows of staple pockets 12.

Figure 15:
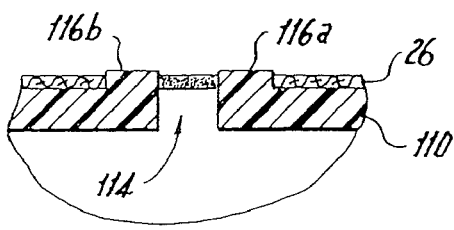
FIG. 15 is a cross sectional view taken along line 15-15 of FIG. 12.

Referring for the moment to FIGS. 11 and 15, cartridge buttress retention system 30 includes a post 116 formed at a distal end 118 of staple containing insert 110. Post 116 is similar to post 76 described hereinabove and is split into halves 116a and 116b to accommodate the passage of a knife blade to sever tissue and cartridge buttress material 26. Cartridge buttress material 26 includes a corresponding hole 20 formed in a distal end 122 of cartridge buttress material and configured to fit over post 116 on staple containing insert 110.

Figure 13:
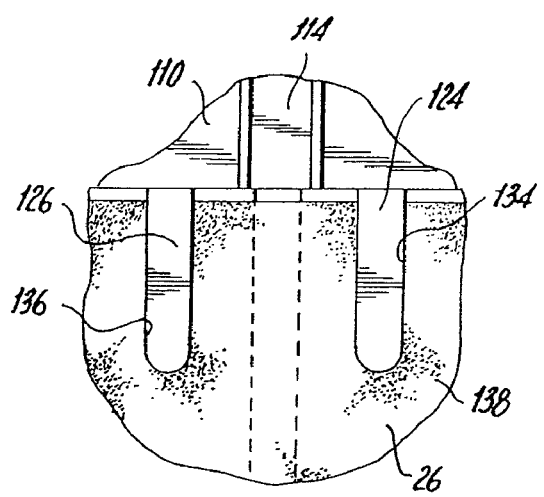
FIG. 13 is a top view of the proximal end of the cartridge buttress retention system of FIG. 12.

Referring back to FIGS. 11 and 12, and with regard to FIG. 13, cartridge buttress retention system 30 further includes a pair of distally extending and relatively straight, spaced apart fingers or projections 124 and 126 formed in a proximal end 128 of staple containing insert 110. Projections 124 and 126 are positioned on either side of knife channel 114 to secure cartridge buttress material 26 adjacent outer edges 130 and 132 of cartridge buttress material 26. Cartridge buttress material 26 is provided with corresponding slots 134 and 136 formed in a proximal end 138 of cartridge buttress material 26. Slots 134 and 136 are configured to engage projections 124 and 126 of staple containing insert 110 in friction fit fashion to retain proximal end 138 of cartridge buttress material 26 on proximal end 128 of staple containing insert 110.

In order to assemble cartridge buttress retention system 30, hole 120 in cartridge buttress material 26 is positioned over protrusion 116 on distal end 118 of staple containing insert 110. Thereafter, proximal end 138 of cartridge buttress material 26 is positioned over proximal end 128 of staple containing insert 110. Slots 134 and 136 in anvil buttress material 26 are forced over projections 124 and 126 on staple containing insert 110 to engage anvil buttress material 26 with staple containing inset 110 in friction fit fashion.

Figure 14:
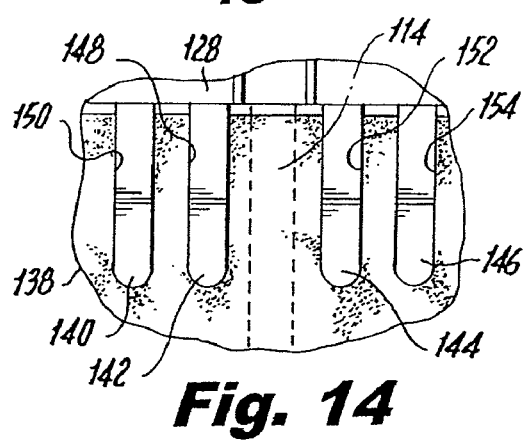
FIG. 14 is a top view of an alternative embodiment of a proximal end of a cartridge buttress retention system.

Referring for the moment to FIG. 14, in an alternative embodiment, proximal end 128 of staple containing insert 110 is provided with multiple sets of fingers or projections 140, 142 and 144, 146 positioned on either side of knife channel 114. Projections 140, 142 and 144, 146 engage corresponding sets of slots 148, 150 and 152, 154, respectively, to secure proximal end 138 of cartridge buttress material 26 to proximal end 128 of staple containing insert 110. By providing multiple sets of fingers on the jaw and corresponding slots in the buttress material, the surface area available for frictional contact is increased providing a more secure connection. While not specifically shown, more than two sets of fingers and slots may be provided depending on the nature of the buttress material and amount of frictional contact required.

Figure 16:
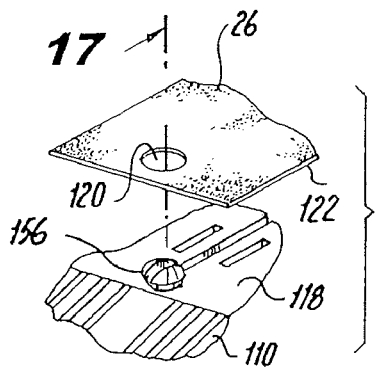
FIG. 16 is a perspective view, with parts separated, of the distal end of the cartridge buttress retentions system of FIG. 12.
Figure 17:
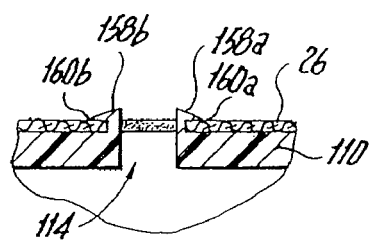
FIG. 17 is a cross-sectional view taken along line 17-17 of FIG. 16.

Referring now to FIGS. 16-21, and initially with regard to FIGS. 16 and 17, alternative methods of releasably securing buttress material to a jaw of a surgical instrument will now be described. A split protrusion 156, similar to protrusion 88 described hereinabove, is formed on a distal end 118 of staple containing insert 110 and includes cap halves 158a and 158b defining flanges 160a and 160b. Hole 120 in distal end 122 of cartridge buttress material 26 fits over split protrusion 156 to secure distal end 122 of cartridge buttress material 26 to distal end 118 of staple containing insert 110.

Figure 18:
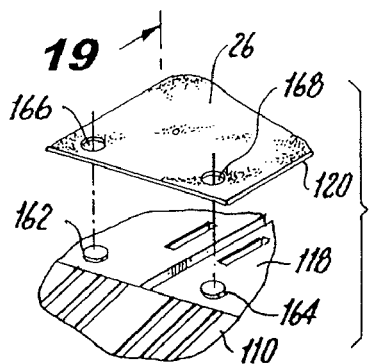
FIG. 18 is a perspective view, with parts separated, of an alternative embodiment of a distal end of cartridge buttress retention system.
Figure 19:
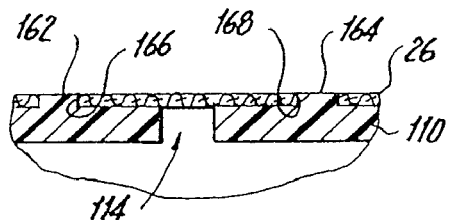
FIG. 19 is a cross-sectional view taken along line 19-19 of FIG. 18.

Referring to FIGS. 18 and 19, distal ends 118 and 120 of staple containing insert 110 and cartridge buttress material 26 may be provided with spaced apart posts 162, 164 and spaced apart holes 166, 168, respectively. Posts 162, 164 and holes 166, 168 function substantially identically to posts 96, 98 and holes 100, 102, described hereinabove, to secure distal end 122 of cartridge buttress material 26 to distal end 118 of staple containing insert 110.

Figure 20:
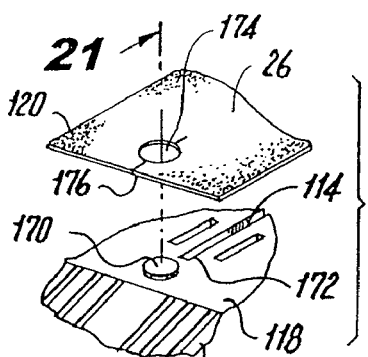
FIG. 20 is a perspective view of, with parts separated, of a further alternative embodiment of a distal end of a cartridge buttress retention system.
Figure 21:
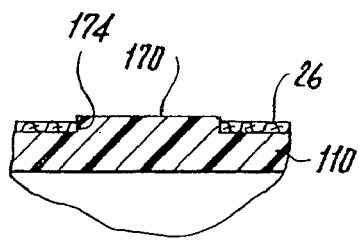
FIG. 21 is a cross-sectional view taken along line 21-21 of FIG. 20.

With respect to FIGS. 20 and 21, a solid, unsplit post 170 is provided on distal end 118 of staple containing insert 110. Post 170 is located distally of a distal end 172 of knife channel 114. A hole 174 is provided in distal end 120 of cartridge buttress material 26 and a longitudinal slit 176 is formed through the area defining hole 174. In use, a knife associated with surgical stapler 10 cuts through cartridge buttress material 26 through the length of knife channel 114. After cartridge buttress material 26 has been stapled to tissue and almost completely been cut in half, longitudinal slit 176 allows cartridge buttress material 26 to separate in half without tearing or snagging.

Figure 22:
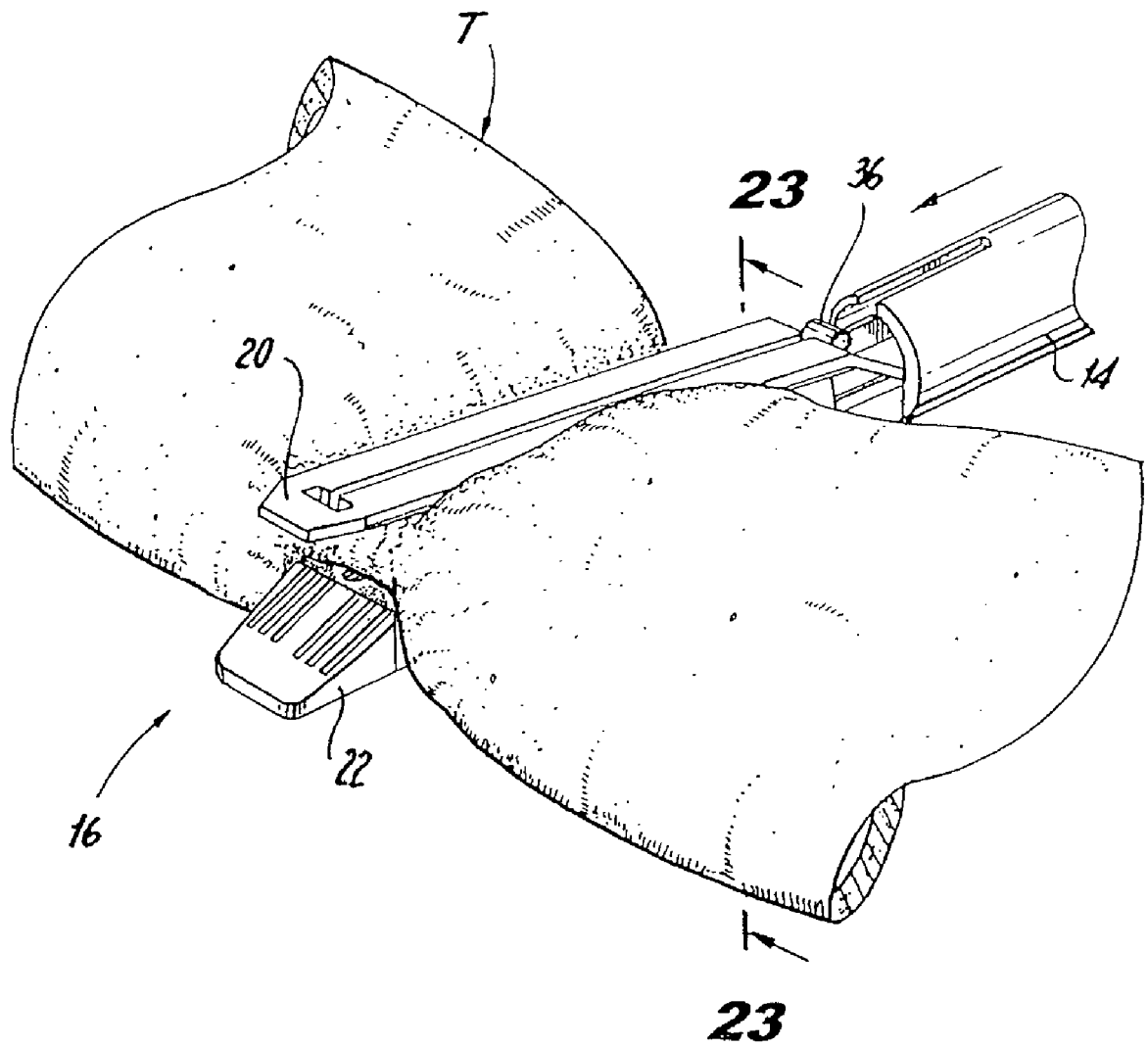
FIG. 22 is perspective view of the distal end of the surgical stapling instrument of FIG. 1 positioned about a tissue section.
Figure 23:
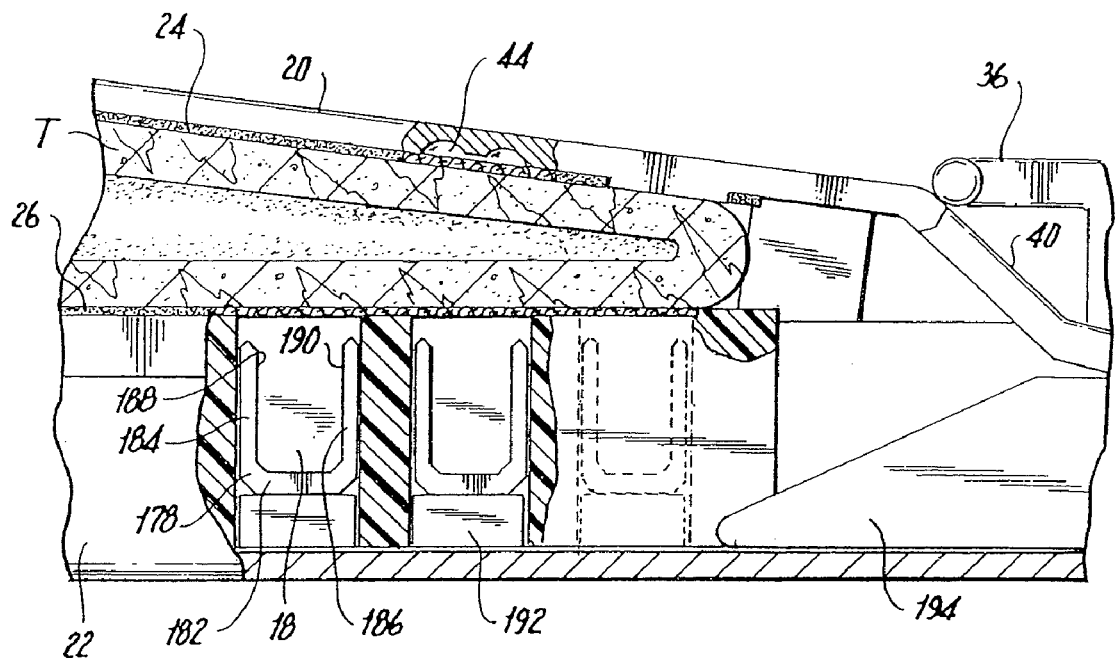
FIG. 23 is side view, partially shown in section, of the distal end of the surgical stapling instrument positioned about the tissue section.

Referring now to FIGS. 22 through 26, and initially with respect to FIGS. 22 and 23, the use of surgical stapler 10 to staple and divide a tubular tissue section T will now be described. Initially, jaw assembly 16, including anvil 20 and staple containing cartridge 22 are positioned around the tissue T to be stapled. Driver 36 is in a proximal position relative to anvil slot 38. As best shown in FIG. 23, staple containing insert 110 includes staples 178 positioned within individual staple pockets 180 of row of staple pockets 112. Staples 178 are of a conventional type and include a backspan 182 having a pair of legs 184 and 186 extending from backspan 182. Legs 184 and 186 terminate in tissue penetrating tips 188 and 190. Pushers 192 are located within staple pockets 180 and are positioned between staples 178 and the path of a drive bar 194.

Figure 24:
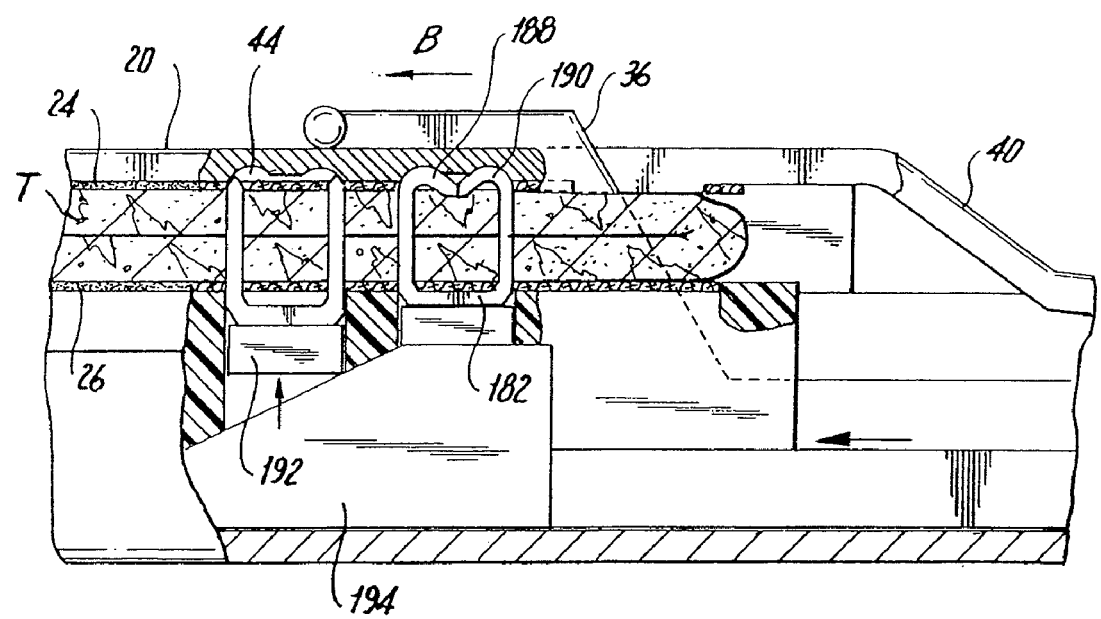
FIG. 24 is a side view, partially shown in section, during initial actuation of the surgical stapling instrument of FIG. 1.

Referring now to FIG. 24, surgical stapler 10 is initially actuated by movement of trigger 32 relative to handle 12 (FIG. 1) causing driver 36 to move in the direction of arrow B and against sloped edge 40 of anvil 20 thereby causing anvil 20 to be moved to the closed position relative to staple cartridge 22. As drive bar 194 advances distally within staple containing insert 110, drive bar 194 urges pushers 192 upwardly against backspans 182 of staples 178 driving staples 178 through cartridge buttress material 26, tissue T, anvil buttress material 24 and towards staple clinching pockets 44 in anvil 20. Tissue penetrating tips 188 and 190 are bent within staple clinching pockets 44 in anvil 20 to thereby secure anvil buttress material 24 against tissue T while backspan 182 secures cartridge buttress material 26 against tissue T.

While not specifically shown, upon full actuation of surgical stapler 10, a knife blade associated with surgical stapler 10 and carried by driver 36 cuts tissue T, as well as anvil buttress material 24 and cartridge buttress material 26 between the rows of now clinched staples 102. Upon movement of anvil 20 to the open position spaced apart from staple cartridge 22, anvil buttress material 24 pulls away from anvil 20 and cartridge buttress material 26 pulls away from staple cartridge 22. Specifically, distal end 122 of cartridge buttress material 26 is cut through by the knife and is released from post 116. Proximal end 138 of cartridge buttress material 26 pulls free from longitudinal projections 124, 126 at proximal end 128 of staple containing insert 110. Likewise, distal end 66 of anvil buttress material 24 pulls free from proximally extending projections 50, 52 and proximal end 82 of anvil buttress material 24 pulls free from post 78.

Figure 25:
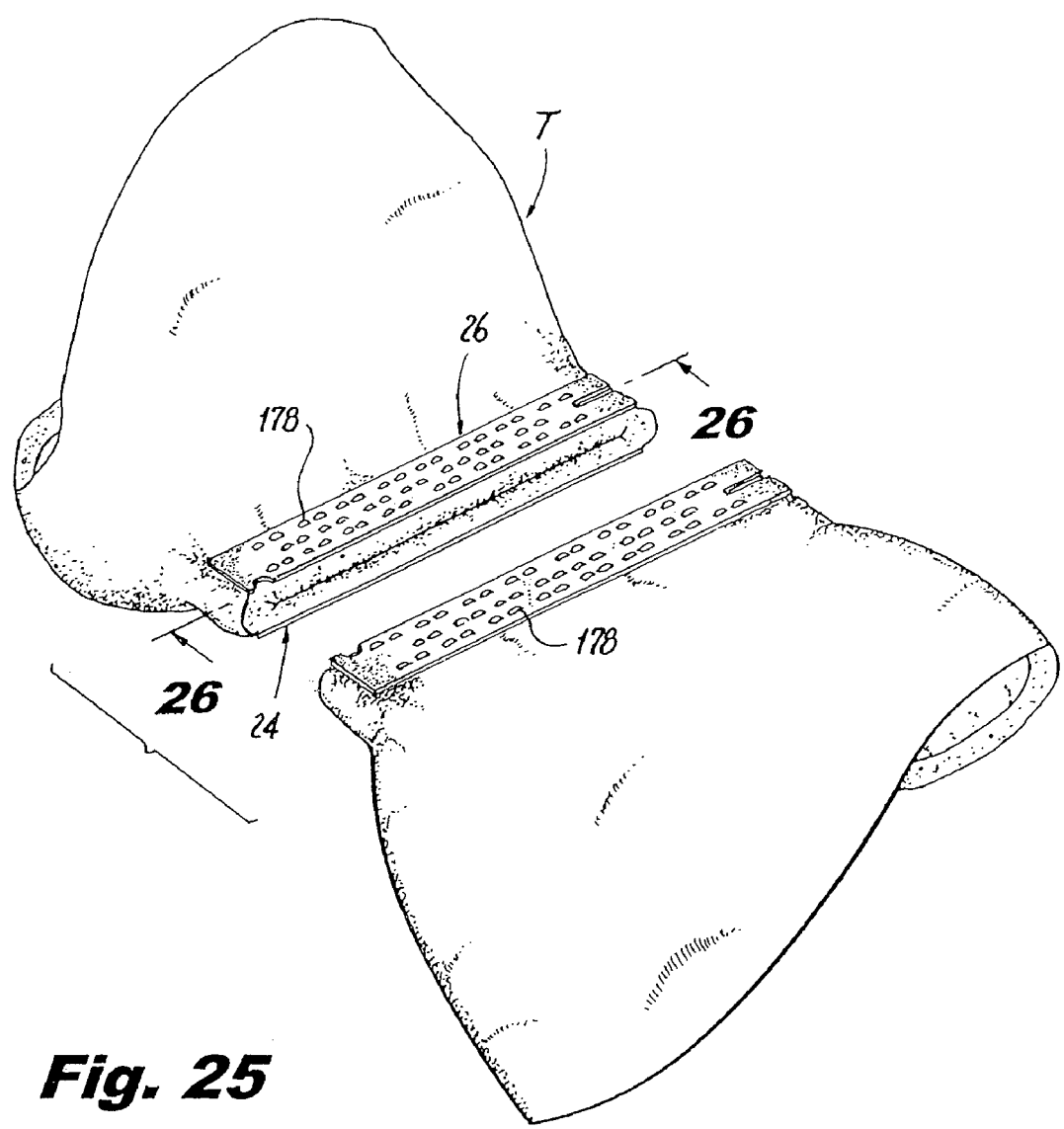
FIG. 25 is a perspective view of a stapled and divided tissue section.
Figure 26:
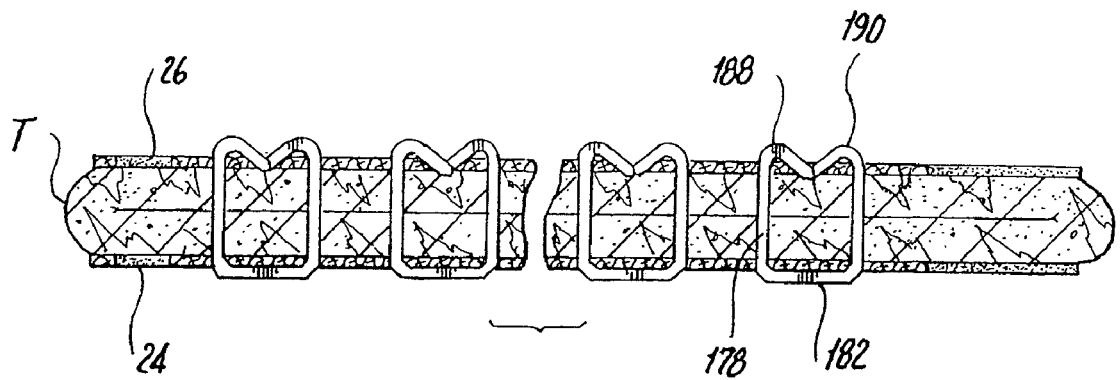
FIG. 26 is a cross-sectional view taken along line 26-26 of FIG. 25.

The resulting tissue T, divided and stapled closed with staples 178, is best illustrated in FIGS. 25 and 26. Specifically, cartridge buttress material 26 is secured against tissue T by backspans 182 of staples 178 and anvil buttress material 24 is secured against tissue T by the now clinched tissue penetrating tips 188 and 190 of staples 178. In this manner, anvil buttress material 24 and cartridge buttress material 26 are stapled to tissue T thereby sealing and reinforcing these staple lines created by staples 178.

Figure 27:
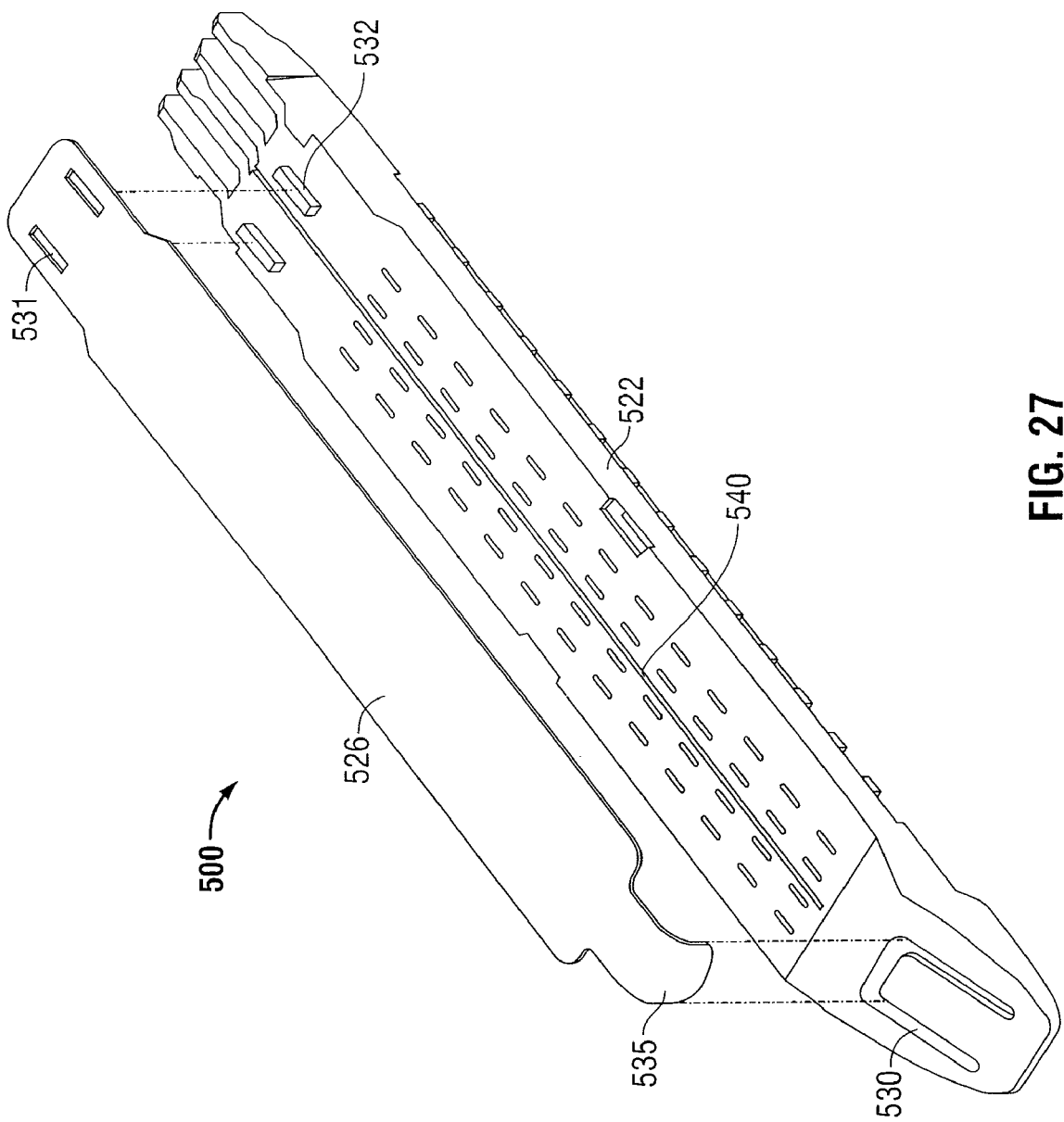
FIG. 27 is a perspective view, with parts separated, of an embodiment of a staple containing cartridge and buttress material retention system.
Figure 28:
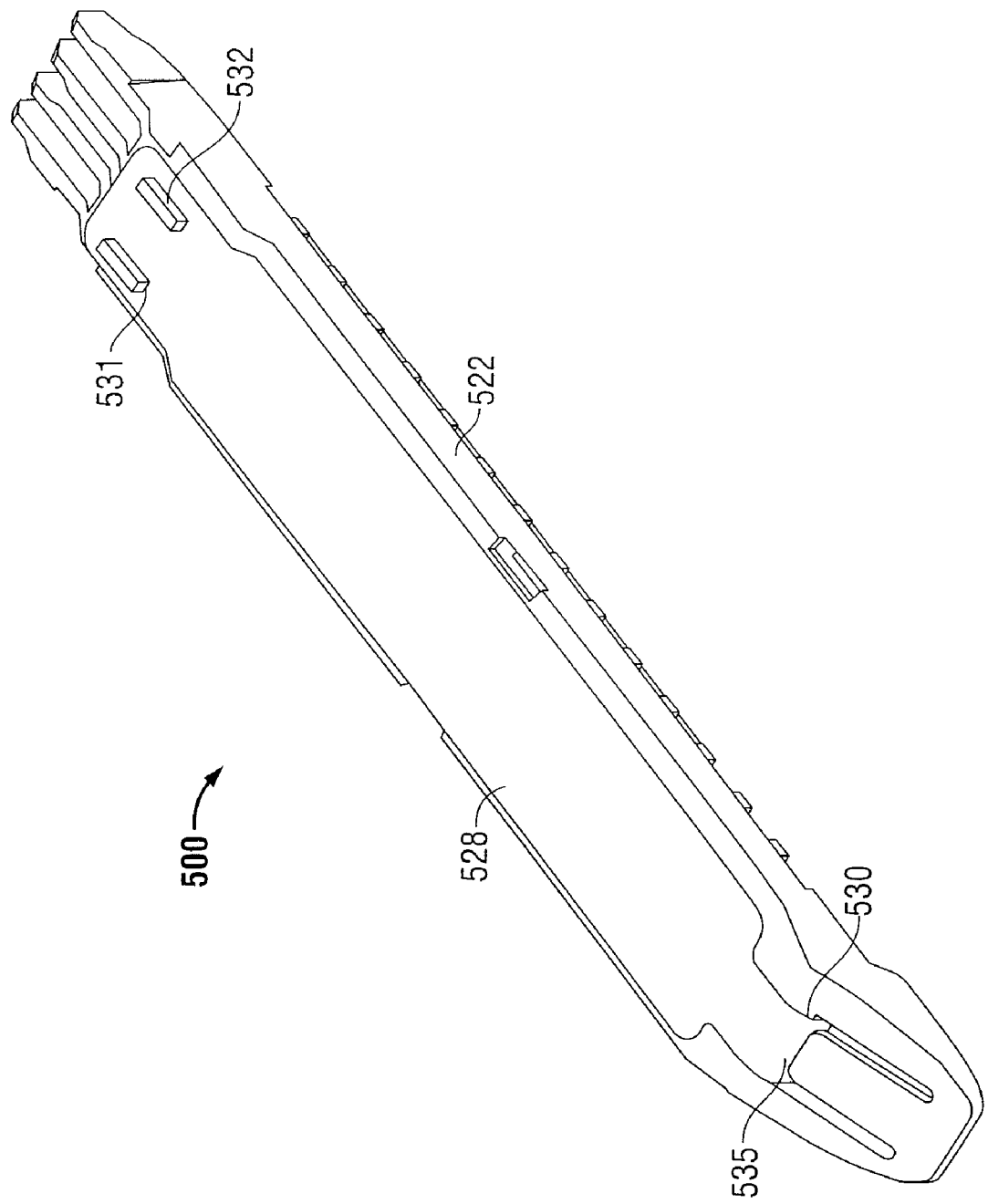
FIG. 28 is a perspective view of the assembled cartridge buttress retention system of FIG. 27.
Figure 29:
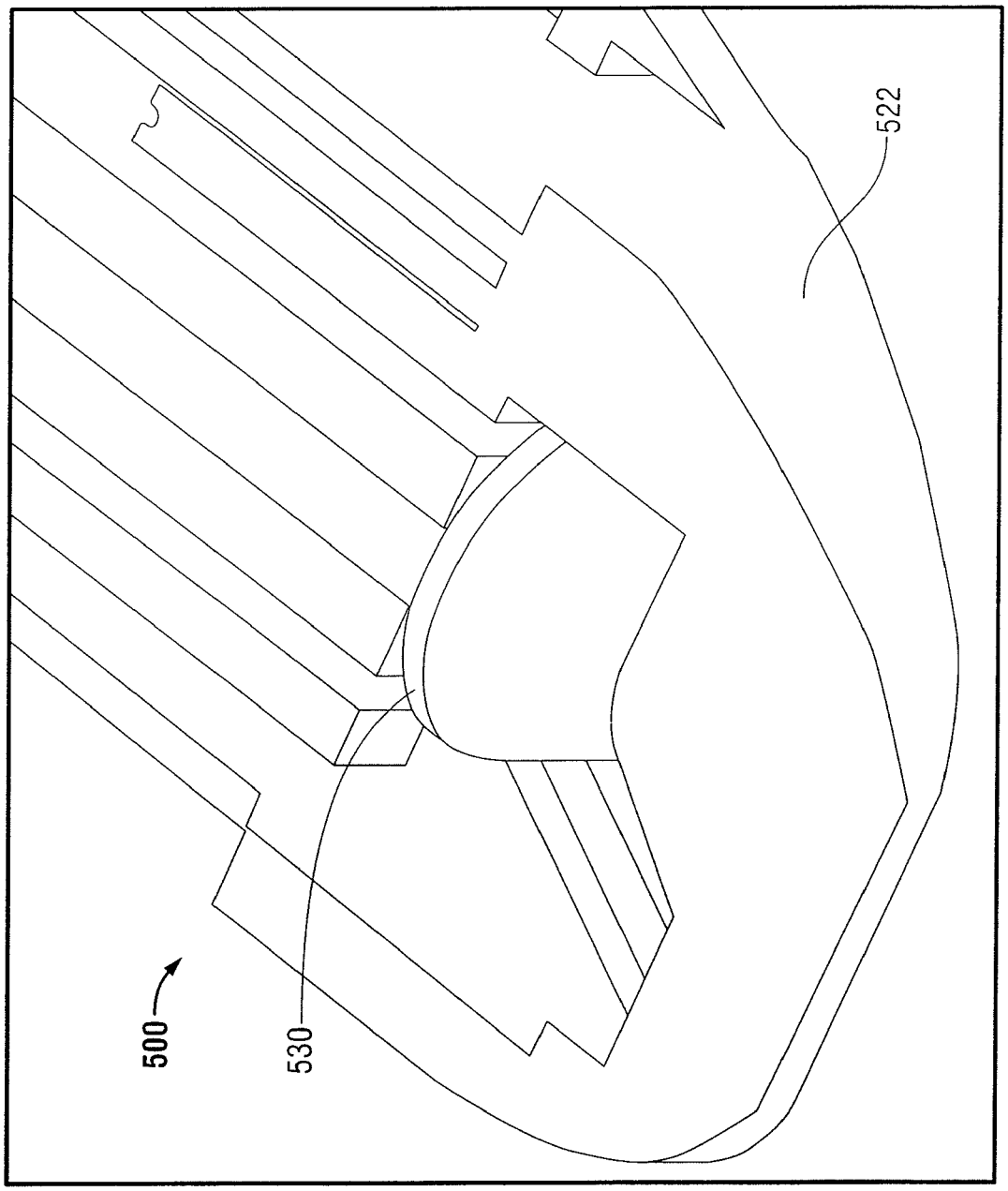
FIG. 29 is a bottom view of the proximal end of the cartridge buttress retention system of FIG. 28.

Referring now to FIGS. 27-29, cartridge retention system 500 will now be described to retain cartridge buttress retention material 526 on a staple cartridge 522 prior to the stapling of tissue. As shown in FIGS. 27 and 28, at least one longitudinally extending projection 532 is positioned at a first end of the staple cartridge 522 and a groove 530 is positioned at a first end thereof. The staple cartridge 522 may include at least two longitudinally extending projections 532, the at least two projections 532 being separated by a knife slot 540. The buttress retention material 526 includes at least one aperture 531 for the receipt of the projections 532 and a tab 535 at a distal end of the buttress retention material 526 configured to engage the groove 530. Tab 535 extends horizontally and distally from the distal end of the buttress retention material 526. Preferably, the tab 535 extends along a central axis of the buttress retention material 526 and has a narrower width relative to a width of the buttress retention material 526. The distal end of the tab 535 curves downwardly to couple with the groove 530 of the staple cartridge. The tab 535 may provide an internal bias or spring action due to the resiliency of the material from which the tab 535 is made. Consequently, when the tab 535 is positioned to engage the groove 530, the tab 535 snaps into a locked position with the groove 530.

FIG. 28 shows the buttress material 528 releasably affixed to the staple cartridge 522. In order to assemble the cartridge buttress retention system 500, apertures 531 are positioned over projections 532 on the first end of the staple cartridge 522. The projections 532 may be slightly larger in size than the apertures 531, thereby providing an interference fit upon insertion of the projections 532 into the apertures 531. The projections 532 and the corresponding apertures 531 may have any geometry best suited for retaining the projections 532 within the apertures 531. The projections 532 may be relatively straight or may have a shape including but not limited to rectangular and cross-shaped geometries. Upon positioning the apertures 531 over the projections 532, the tab 535 of the buttress retention material 526 is positioned over the groove 530. Once so positioned, the tab 535 is forced over the groove 530, as shown best in FIG. 29, thereby securing the buttress retention material 526 to the staple cartridge 522. An audible indicator, e.g., a clicking sound, may confirm placement of the buttress retention material 526 on the staple cartridge 522.

Figure 30A:
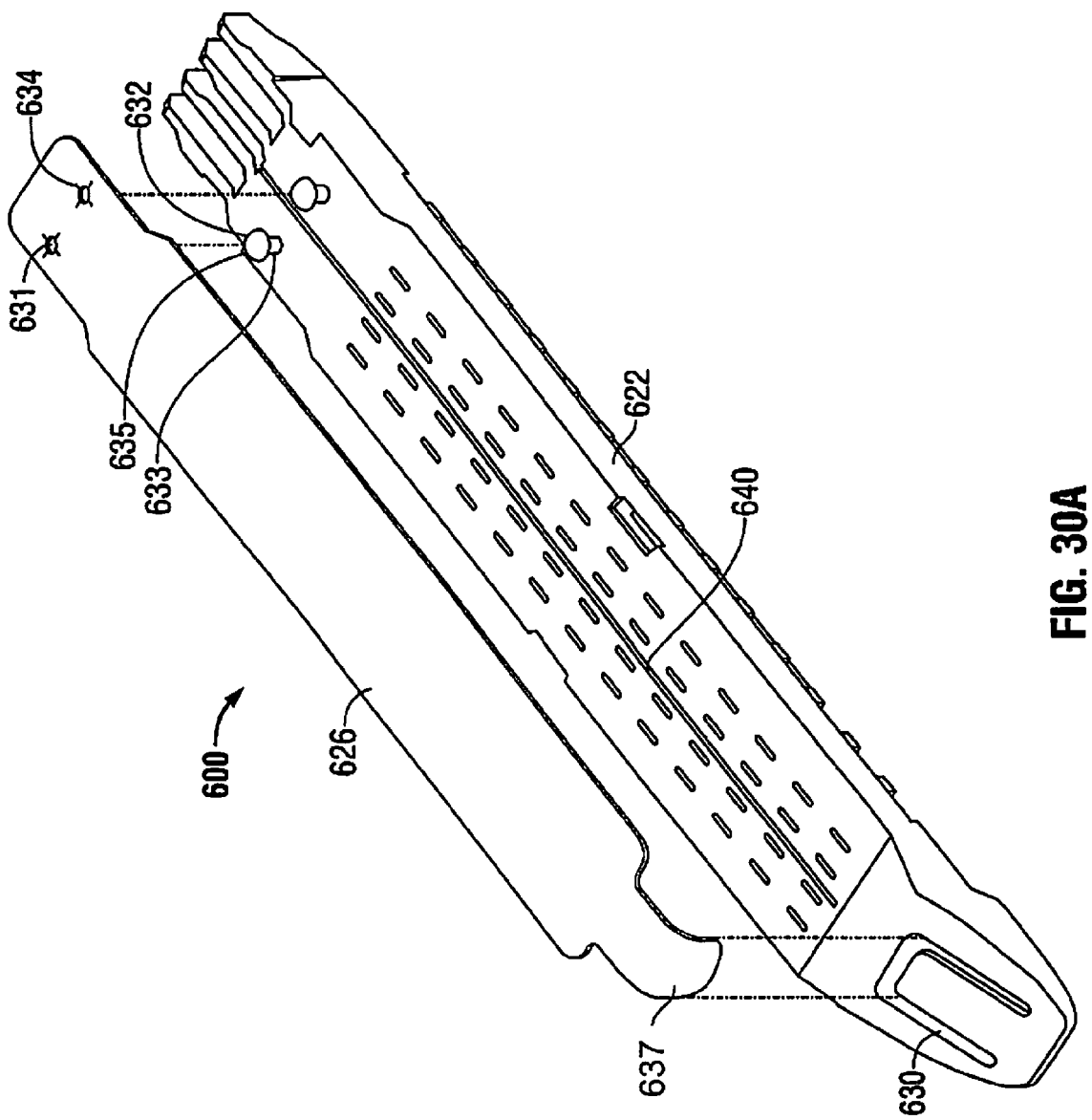
FIG. 30A is a perspective view of the distal end of the cartridge buttress system, with parts separated, of an embodiment of a staple containing cartridge and buttress material retention system.
Figure 30B:
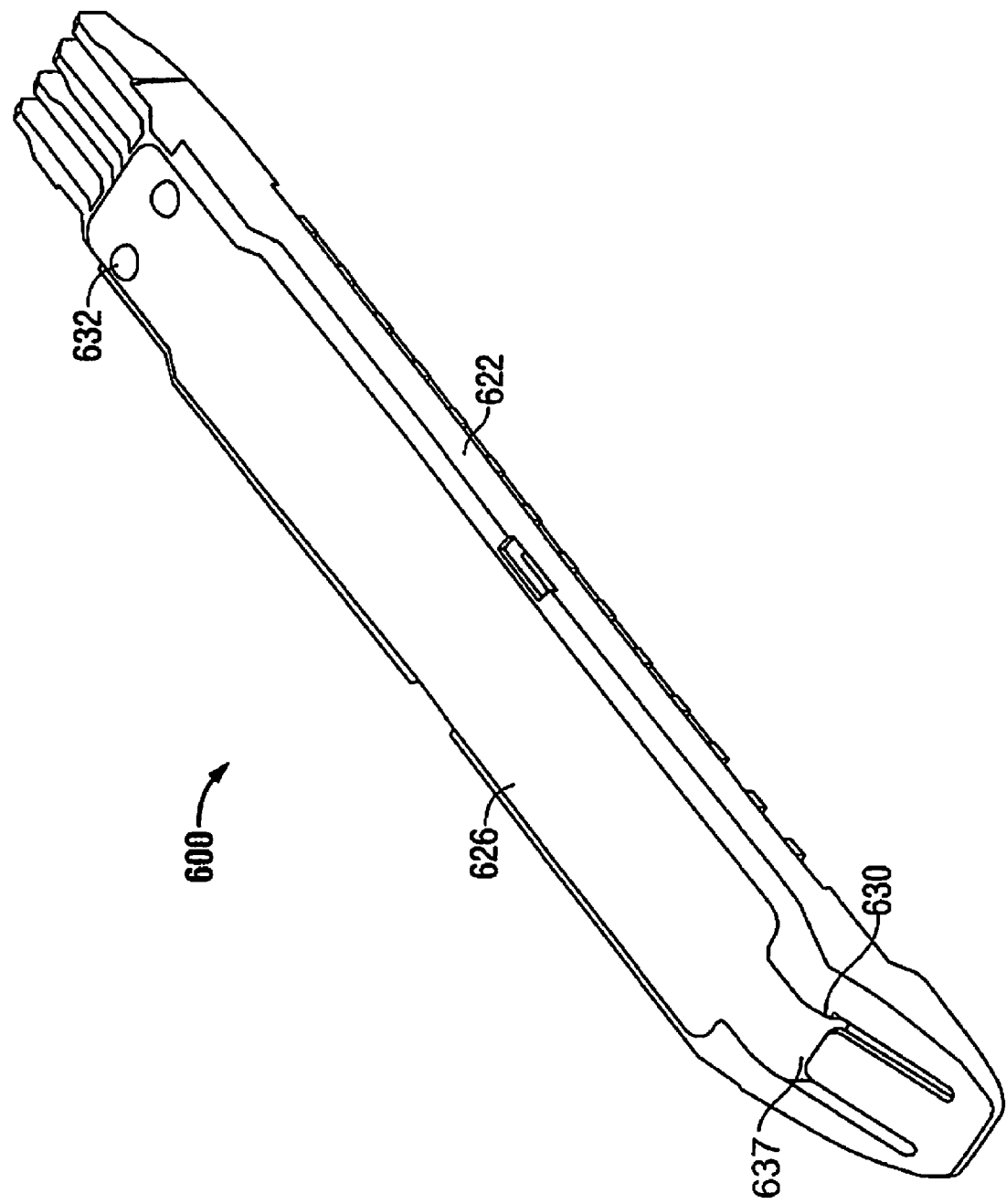
FIG. 30B is a perspective view of the assembled cartridge buttress retention system of FIG. 30A.

In a further embodiment, shown in FIGS. 30A and 30B, a buttress retention system 600 is provided including a buttress retention material 626 and a staple cartridge 622. The buttress retention material 626 includes apertures 631 adapted to receive one or more projections 635, the projection 635 including a bulbous head 632 and a neck portion 633. The staple cartridge 622 may include at least two projections 635, the at least two projections 635 being separated by a knife slot 640. A slit 634 may extend longitudinally from the aperture 633 to prevent tearing or snagging upon insertion of the projection 635 into aperture 633. A tab 637 at an end of the buttress retention material 626 is engagable with a groove 630 at an end of the staple cartridge 622.

It will be understood that various modifications may be made to the embodiments disclosed herein. For example, various numbers of interlocking fingers or projections may be provided to increase the frictional contact between a jaw and an associated buttress material. Further, the disclosed buttress materials may be provided with various perforated regions to facilitate release from the disclosed fingers or projections and posts. Therefore, the above description should not be construed as limiting, but merely as exemplifications of particular embodiments. Those skilled in the art will envision other modifications within the scope and spirit of the claims appended hereto.

What is claimed is:

1. A staple cartridge, comprising:
a housing including a proximal portion and a distal portion, the housing defining a surface including a plurality of staple pockets formed in a tissue contacting surface thereof for the reception of staples therein; and
a buttress material including a proximal and a distal portion, the buttress material releasably securable to the surface of the housing atop of the staple pockets, the distal portion of the buttress material defining a distal end having a tab extending distally therefrom, the tab having a narrower width relative to the buttress material and the distal portion of the housing defining a groove, the tab configured to be releasably secured to the groove.

2. The staple cartridge of claim 1, wherein the tab is friction fit into the groove.

3. The staple cartridge of claim 1, further comprising a knife blade and a knife channel, the knife blade receivable through the knife channel.

4. The staple cartridge of claim 3, wherein the buttress material overlies the knife channel.

5. The staple cartridge of claim 4, wherein the knife blade severs the buttress material as the knife blade travels through the knife channel.

6. The staple cartridge of claim 3, wherein the groove is disposed distal of the knife channel and wherein the tab is friction fit within the groove.

7. The staple cartridge of claim 1, wherein the staple cartridge includes at least one projection extending from the tissue contacting surface, and wherein the buttress material includes at least one aperture for receiving a respective one of the at least one projection.

8. A staple cartridge, comprising:
a housing including a proximal portion and a distal portion, the housing defining a surface including a plurality of staple pockets formed in a tissue contacting surface thereof for the reception of staples therein, wherein the distal portion of the housing defines a groove and wherein the housing includes at least one projection extending from the tissue contacting surface; and
a buttress material including a proximal and a distal portion, the buttress material releasably securable to the surface of the housing atop of the staple pockets, the distal portion of the buttress material defining a distal end having a tab extending distally therefrom, the tab having a narrower width relative to the buttress material, the tab configured to be releasably secured in the groove, and wherein the buttress material includes at least one aperture for receiving a respective one of the at least one projection.

9. The staple cartridge of claim 8, wherein the tab is friction fit into the groove formed in the housing of the staple cartridge.

10. The staple cartridge of claim 9, wherein the groove is disposed distal of the knife channel and wherein the tab is friction fit within the groove.

11. The staple cartridge of claim 8, further comprising a knife blade and a knife channel, the knife blade receivable through the knife channel.

12. The staple cartridge of claim 11, wherein the buttress material overlies the knife channel.

13. The staple cartridge of claim 12, wherein the knife blade severs the buttress material as the knife blade travels through the knife channel.

14. A surgical stapler, comprising:
a handle; and
an end effector connected to the handle assembly and operable by the handle, the end effector supporting a replaceable staple cartridge, the staple cartridge including:
a housing including a proximal portion and a distal portion, the housing defining a surface including a plurality of staple pockets formed in a tissue contacting surface thereof for the reception of staples therein; and
a buttress material including a proximal and a distal portion, the buttress material releasably securable to the surface of the housing atop of the staple pockets, the distal portion of the buttress material defining a distal end having a tab extending distally therefrom, the tab having a narrower width relative to the buttress material and the distal portion of the housing defining a groove, the tab configured to be releasably secured to the groove.

15. The surgical stapler of claim 14, wherein the staple cartridge includes a first end and a second end, at least one projection extends from the first end of the staple cartridge, the groove is positioned at the second end of the staple cartridge, the buttress material includes at least one aperture at a proximal end for the reception of the at least one projection therein, the buttress material includes at least one tab at a distal end of the buttress material, the at least one tab is friction fit into the groove of the staple cartridge.

16. The surgical stapler of claim 14, wherein the buttress material defines a tab that is friction fit into the groove formed in the housing of the staple cartridge.

17. The surgical stapler of claim 14, wherein the surgical stapler includes a knife blade and the stapler cartridge defines a knife channel, the knife blade receivable through the knife channel.

18. The surgical stapler of claim 17, wherein the buttress material overlies the knife channel.

19. The surgical stapler of claim 17, wherein the knife blade is actuatable by the handle and severs the buttress material as the knife blade travels through the knife channel.

* * * * *